United States Patent
Djachiachvili

(10) Patent No.: US 8,860,802 B2
(45) Date of Patent: Oct. 14, 2014

(54) METHOD AND APPARATUS FOR DETECTING DEFECTS AND EMBEDDED OBJECTS IN SEALED STERILIZED PACKAGING

(76) Inventor: Youri N. Djachiachvili, Albuquerque, NM (US)

( * ) Notice: Subject to any disclaimer, the term of this patent is extended or adjusted under 35 U.S.C. 154(b) by 748 days.

(21) Appl. No.: 12/575,904

(22) Filed: Oct. 8, 2009

(65) Prior Publication Data

US 2010/0118138 A1 May 13, 2010

Related U.S. Application Data

(60) Provisional application No. 61/104,203, filed on Oct. 9, 2008.

(51) Int. Cl.
- *H04N 7/18* (2006.01)
- *G01N 21/94* (2006.01)
- *G01N 21/95* (2006.01)
- *G01N 21/90* (2006.01)

(52) U.S. Cl.
CPC ........ *G01N 21/95* (2013.01); *G01N 2201/0833* (2013.01); *G01N 21/94* (2013.01); *G01N 21/9018* (2013.01)
USPC ............. 348/125; 348/92; 348/127; 382/141; 382/142; 382/143

(58) Field of Classification Search
USPC ...................... 348/92, 125, 127; 382/141–143
See application file for complete search history.

(56) References Cited

U.S. PATENT DOCUMENTS

| | | | |
|---|---|---|---|
| 3,932,042 A * | 1/1976 | Faani et al. | 356/239.4 |
| 3,966,332 A * | 6/1976 | Knapp et al. | 356/427 |
| 4,037,724 A | 7/1977 | Schultz et al. | 209/111.7 R |
| 4,441,817 A * | 4/1984 | Pryor | 356/615 |
| 4,672,437 A | 6/1987 | Casper | 358/101 |
| 4,760,421 A | 7/1988 | Margolin | 355/1 |
| 4,972,494 A | 11/1990 | White et al. | 382/8 |
| 5,072,108 A * | 12/1991 | Ishikawa | 250/223 B |
| 5,155,790 A | 10/1992 | Hwang | 385/121 |
| 5,320,814 A | 6/1994 | Walt et al. | 422/82.07 |
| 5,515,159 A * | 5/1996 | Sites et al. | 356/237.1 |
| 5,701,178 A * | 12/1997 | Burns et al. | 356/600 |
| 6,091,872 A | 7/2000 | Katoot | 385/116 |
| 6,097,427 A * | 8/2000 | Dey et al. | 348/92 |
| 6,417,506 B1 | 7/2002 | Pinkel et al. | 250/216 |
| 7,060,981 B2 | 6/2006 | Retterath et al. | 250/359.1 |
| 7,162,073 B1 | 1/2007 | Akgul et al. | 382/149 |
| 7,271,381 B2 | 9/2007 | Arnold et al. | 250/227.11 |
| 7,771,776 B2 * | 8/2010 | Furze et al. | 427/9 |
| 2005/0180699 A1* | 8/2005 | Shu et al. | 385/89 |
| 2005/0224724 A1* | 10/2005 | Hubert Jacobus Carpaij et al. | 250/492.22 |
| 2010/0013500 A1* | 1/2010 | Maher et al. | 324/663 |
| 2010/0020927 A1* | 1/2010 | Gilevich et al. | 378/57 |

* cited by examiner

*Primary Examiner* — Duyen Doan
(74) *Attorney, Agent, or Firm* — Luis M. Ortiz; Kermit D. Lopez; Ortiz & Lopez, PLLC

(57) ABSTRACT

An inspection station identifies defects such as artifacts (e.g., dust, hair, particles) in the sealing areas of sealed sterile packages. A multi-head optical scanner can include at least two fiber optic sensors each comprised of a bundle of optical fibers arranged into a linear face coupled to an image processing module and oriented towards a scanning area of sealed packages moving through a conveyance system. An image processing module can analyze input from the at least two fiber optic sensor arrangements to identify artifacts in the sealing areas of the sealed packages.

11 Claims, 4 Drawing Sheets

```
┌─────────────────────────────────────────────┐
│  OPTICALLY CAPTURING IMAGES OF SEALING      │  410
│  AREAS ON SEALED STERILE PACKAGES USING A   │
│  MULTI-HEAD OPTICAL SCANNER INCLUDING AT    │
│  LEAST TWO FIBER OPTIC SENSORS EACH         │
│  COMPRISED OF BUNDLE OF OPTICAL FIBERS      │
│  COUPLED TO AN IMAGE PROCESSING MODULE      │
│  AND ORIENTED TOWARDS A SCANNING AREA OF    │
│  SEALED PACKAGES MOVING THROUGH A           │
│  CONVEYANCE SYSTEM                          │
└─────────────────────────────────────────────┘
                      │
                      ▼
┌─────────────────────────────────────────────┐
│  PROCESSING IMAGES OF SEALING AREAS         │  420
│  CAPTURED BY THE MULTI-HEAD OPTICAL         │
│  SCANNER TO DETERMINE IF THE SEALING        │
│  AREAS CONTAIN ARTIFACTS THEREIN            │
└─────────────────────────────────────────────┘
                      │
                      ▼
┌─────────────────────────────────────────────┐
│  IDENTIFYING SEALING AREAS INCLUDING        │  430
│  SEALING AREA LOCATIONS WHEREIN ARTIFACTS   │
│  ARE LOCATED WITHIN SEALED STERILE          │
│  PACKAGES                                   │
└─────────────────────────────────────────────┘
```

FIG. 4

METHOD AND APPARATUS FOR DETECTING DEFECTS AND EMBEDDED OBJECTS IN SEALED STERILIZED PACKAGING

INVENTION PRIORITY

The present invention claims priority of Provisional Patent Application No. 61/104,203, filed Oct. 9, 2008, entitled "method and apparatus for detecting defects and embedded objects in sealed sterilized packaging," which is hereby incorporated by reference.

TECHNICAL FIELD OF THE INVENTION

The embodiments of the invention are generally related to the field of automated packaging processes, and in particular, to sterilized packaging. More particularly, the embodiments of the invention are related to methods, systems and apparatuses for detecting defects and embedded object in sealed, sterilized packaging within an automated system and process.

BACKGROUND OF THE INVENTION

The present invention relates to the quality control of the sealed sterile packaging process. Various micro objects (e.g., human hair, dust, injection molding debris, etc.) can become embedded between sealing surfaces, which can compromise the sealing of sterile surgical instruments in a sterile package. It is desirable to automatically identify defective package sealing products since the use of human operators to perform this task is costly and unreliable.

While the largest defects (discontinuities or voids) can be found using a conventional optical inspection system such as that described in U.S. Pat. No. 6,097,427, issued Aug. 1, 2000, by taking an video image of sealing areas, it is difficult to recognize micro defects or embedded objects with characteristic dimensions less than a hundred microns on large inspection areas during manufacturing process. Attempts to increase magnification of the optical system to increase object resolution will cause decreasing the camera field area resulting in impractical images, long processing time, or complex visual system setups.

U.S. Pat. No. 5,155,790 issued Oct. 13, 1992, describes an electronic scanner or printer with fiber optic bundles. This system uses unique optical fiber bundles for the optical subassembly to transfer images. The fiber bundle is organized so that first face (scanner) has a linear geometry and the second face has area geometry. In the scanner configuration the fiber optic linear bundle transmits image pixels to the face, which is then mechanically scanned into the video system and memory for future image processing. The linear face comprises nominally 5100 square fibers that covers up to 8.5 inches of a document with the fiber core diameter being about eight microns. Such a scanner, however, cannot be applied to the scan packaging area for several reasons: the scanning area is not flat and its scanning speed is too slow for real time defects detection.

What is needed in the packaging art are improved methods and systems for detecting defects and contamination (e.g., embedded objects) in sealed, sterilized packaging before it is shipped from packaging operations to customers.

SUMMARY OF THE PRESENT INVENTION

The following summary is provided to facilitate an understanding of some of the innovative features unique to the disclosed embodiment and is not intended to be a full description. A full appreciation of the various aspects of the embodiments disclosed herein can be gained by taking the entire specification, claims, drawings, and abstract as a whole.

It is a feature of the present invention to enable improved quality control over sealed sterilized packaging process.

It is another feature of the present invention to provide systems and methods that can obtain high resolution images at important regions (e.g., sealing paths) of packages and that is, therefore, simple to implement and operate with low equipment costs (e.g., eliminating the need of multiple cameras).

It is another feature of the present invention to use the multi-head fiber optical scanner for parallel image processing of all regions of interest during single frame capture of sampled packaging.

Accordingly, it is a feature of the present invention to utilize a set of linear fiber optic arrays distributed along the sealing paths of a sterile package as the "scanned area"to dynamically acquire pixels at a stacked linear array face. Each column (or row) provides a remote optical transmission of light illumination from the scanned area, while the whole stack produces a 2×d matrix for a whole set of fiber optic pixel image from the different locations on the package area. This method provides highly effective, parallel image processing, and an optimum procedure to scan sealing packaging areas using a single high-resolution camera. As an additional feature, fiber optic sensors can be oriented at certain angles over the scanning direction of a package to cover larger detection width over the target package.

BRIEF DESCRIPTION OF THE DRAWING

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 4 is a flow diagram of a method of inspecting sealed sterile packaging for artifacts, in accordance with features of the present invention.

DETAILED DESCRIPTION OF THE PREFERRED EMBODIMENT

The particular values and configurations discussed in these non-limiting examples can be varied and are cited merely to illustrate at least one embodiment and are not intended to limit the scope thereof.

Figure 1:
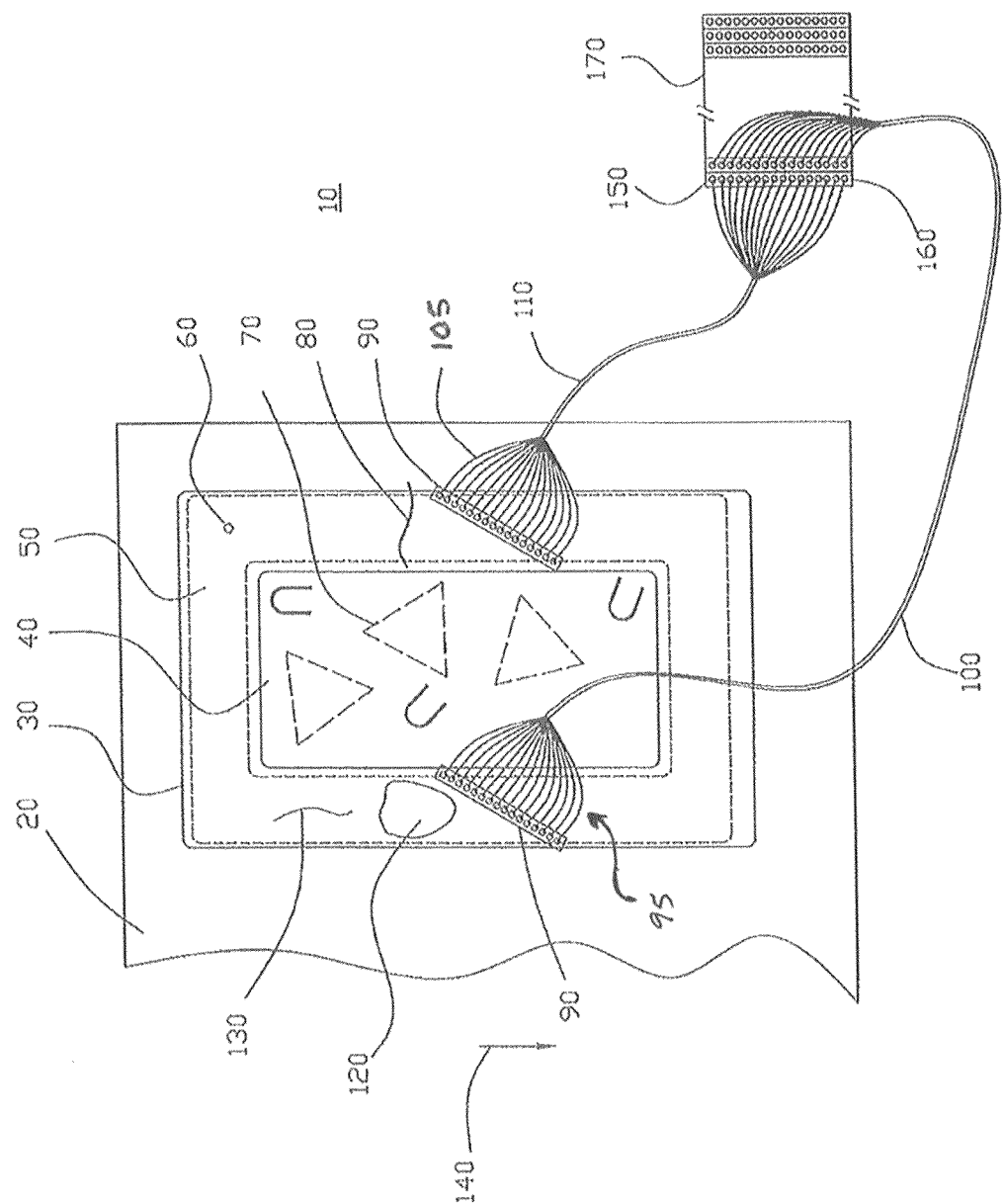
FIG. 1 is a schematic diagram of fiber optical subassembly on the sealing area in accordance to the principles of this invention.

FIG. 1 is a schematic illustration of the multi-head optical scanner 10 employing fiber optic sensor arrangements 90 (e.g., an array) for transmitting optical energy. Each sensor 95, 105 is comprised of bundle of optical fibers 100, 110 arranged in a linear face 90 oriented towards a scanning area (or areas) of a package 20. As an example, the package 20 illustrated in FIG. 1 includes a sterile area including a sealed pocket 40 defined by a border 30 and includes a sealing area 50. Sterile objects (e.g., surgical tools) 70 are contained within the pocket 40. Input from the sensors 90 can be combined together into 2×D area face 170. In the illustrated embodiment, the multi-head optical scanner is shown with only two stationary sensors 95, 105 that could perform a scan of the sealing area 50 when the package 20 is moving along axis 140 along a package conveyance system (not shown); although it can be appreciated that more (or less) sensors can be employed, depending on the application. The sensors 95,105 can be positioned at small 0.5 mm to 1 mm focal distances from the sealing surface and can have about a 30 degree angular position towards the direction of package motion to cover all width of a sealed pocket 40 defined by the sealing area 50. A fiber optic bundle 100 can be operative to transmit pixels that represent sealing surface illumination around the fiber cores. Signals from the sensor can be provided by the area face image processing module for processing and the identification of artifacts in the scanned areas. A controller coupled to the processing module can provide a control signal to identify a faulty package once artifacts in a sealing area 50 are identified.

For illustration purpose only several types of defects are shown in the sealing area 50, but only two of them 80 and 120 can likely compromise the sealed pocket's sealing. The other embedded objects 60 and 130 are not likely to breach the seal because of their orientation and size, respectively. Each column 150, 160 within the 2×D structure of the area face 170 represents pixel images from certain location of a target package (in this case the sealing area 50) during the package's 20 motion 140 (e.g., motion along an automated inspection line). The system 10 and its method of use allow parallel image processing during package inspection from multiple sensors during a single camera frame acquisition, which is a great advancement over the current state of the art.

Figure 2:
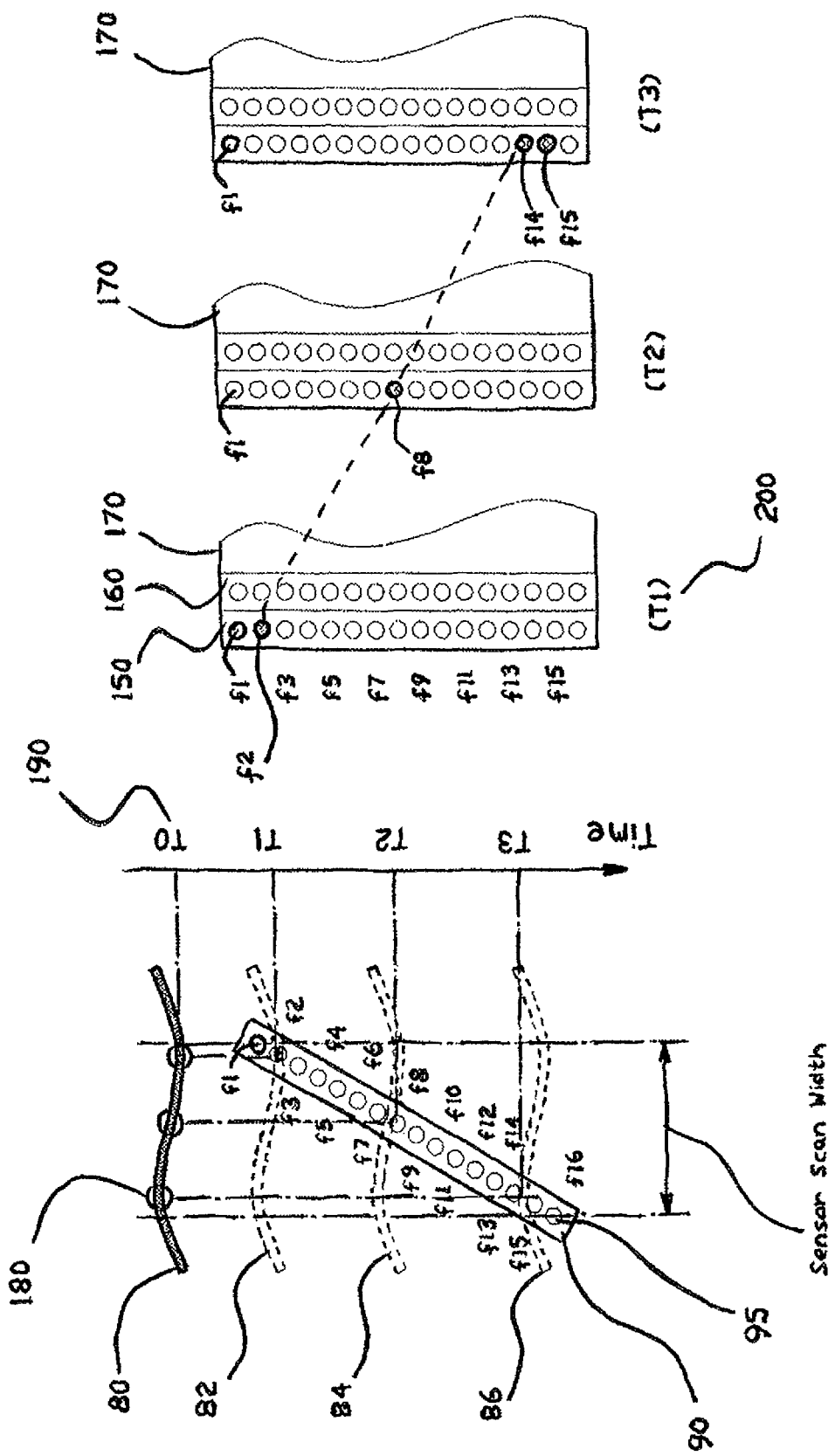
FIG. 2 is a schematic illustration of embedded object detection method during scanning of the sealing area by single linear array sensor for three sequential video frames.

FIG. 2 shows a schematic representation of the linear fiber optic sensor arrangement 90 used during image registration of embedded object 80 for three sequential frames. For reliable pixels detection, diameter of the fiber core can ideally not exceed more than 25% of the characteristic size of embedded object. In one test embodiment the 65 μm fiber core 95 of 1×16 linear sensors is using to detect a human hair of 50 μm, the core fibers being separated in array by 5 to 10 microns. Instantaneous object 80 (e.g., a human hair) positions are shown during frame translations 200 shown at moments in time T1, T2, and T3 during sequential camera frames registrations. Positions are further represented by object spatial positions in FIG. 2 by references 82, 84, and 86. As can be seen the object registers first at fiber f2 (time mark T1), then at fiber f8 (time mark T2), and finally f14 and f15 (time mark T3). Time interval (T2−T1, or T3−T2) between object registrations depends on chosen camera frame rate that has to be high enough to provide at least three frames per an embedded object registration in order to reliably distinguish the object motion. First and second frames will capture illumination from single fibers f2 and f8 while the third frame registers pixels in fibers f14 and f15 resulting in spatial pixels distance in fiber bundle 150 of 2×D area face that projected into camera photosensitive CCD. Pixel translations can be easily recognized during image processing, thus producing a signal to a PLC 280 to reject corresponding pocket 40 in the package 20.

Figure 3:
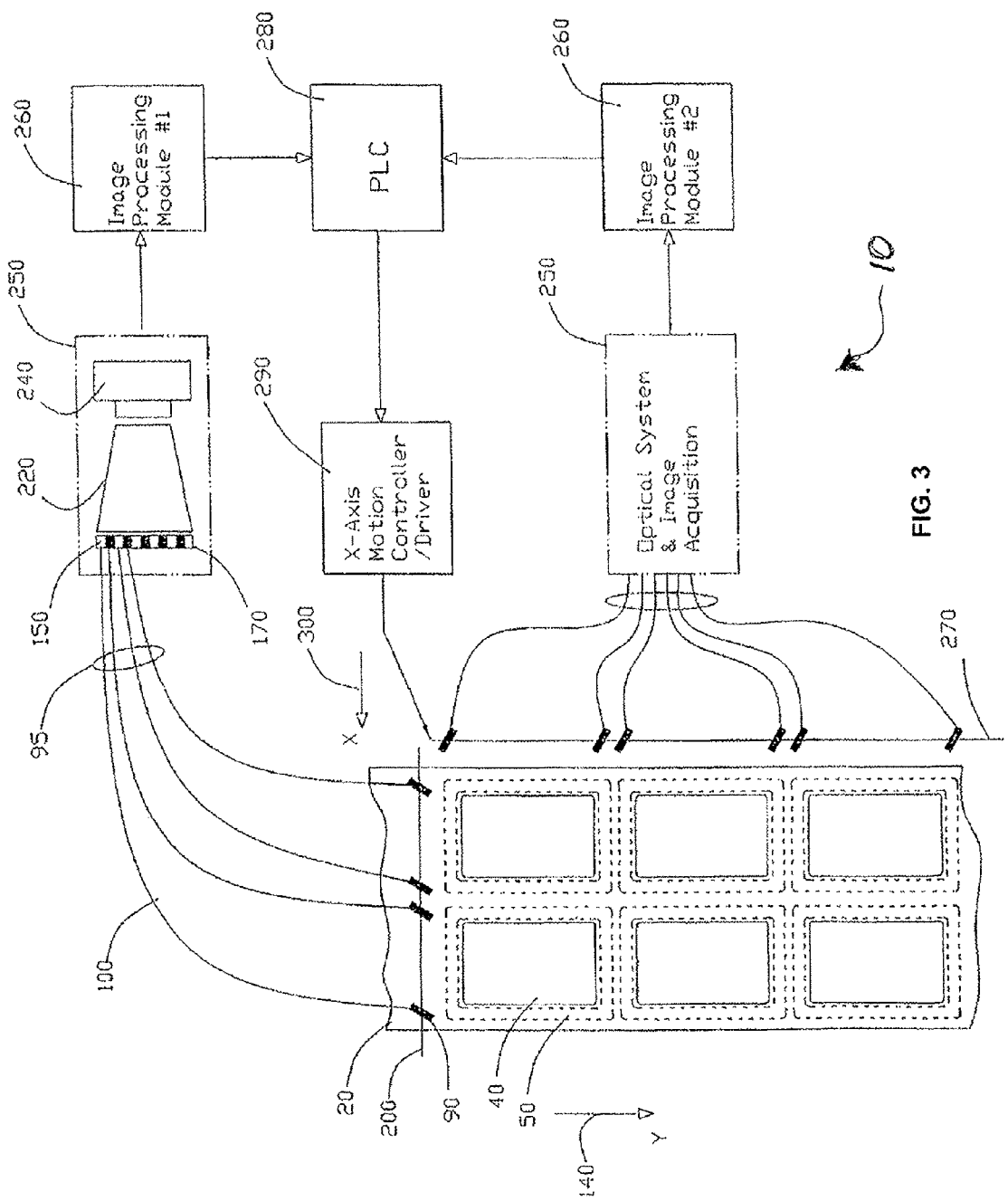
FIG. 3 is a plan view of six sealed sterile surgical packets in a package frame and a block diagram of the vision and control systems associated with the present invention.

FIG. 3 illustrates an embodiment of a system for detecting embedded micro objects in a sealing area of a sterile package. Illustrated for exemplary purposes is a frame 20 of six sealed sterile packages 40 being processed through a defect inspection system 10. The system 10 includes two set of linear optical sensors 200 and 270. The packages can be provided in two rows (three per row) in a common frame 20. The first set of optical sensors can be positioned on a fixed bar where each sensor is aligned with the sealed areas 50 along the entire package frame 20. A second set of optical sensors can be mounted on a movable axis 270 that provides scanning of sealed areas 50 along a second direction 300, which is shown in FIG. 3 as perpendicular to the motion of a conveyance system (not shown). Both sets of sensors 200, 270 provide complete sealed area package inspection. Accordingly, the first set performs defects inspection while conveyer is at motion along direction 140 and the second set of sensors 270 can be activated the when conveyer is stopped for parts loading in upstream of conveyer.

Two sets of linear fiber optic sensors are combined into area face 150 in an optical system 250 forming 2×D image of scanning areas between sealed packages as shown in FIG. 3. Pixel images captured by the fiber face area can be coupled to a camera CCD chip 240 by fiber optic taper 220. A fiber optic taper is an off-shelf optical component, which is a coherent fiber optic plate that transmits either a magnified or reduced image from its input surface to its output surface. The output of the optical system 250 can be connected to an image processing module 260, where frame-by-frame image analysis can be performed, either in real time, or using set of buffered images, to search a pre-defined defects pattern. When defect has being detected by the image processing module 260, a fault condition can be generated by a PLC 280. The fault condition (a signal) from the PLC can be used to identify the compromised package so that it can be removed or marked for rejection. As an example, the PLC 280 can send a signal downstream to the frame unload station to identify (mark) fault or to automatically separate defective product from the good product.

Referring to FIG. 4, a flow diagram of a method of inspecting sealed sterile packaging for artifacts is illustrated. As shown in block 410, the method begins by optically capturing images of sealing areas on sealed sterile packages using a multi-head optical scanner including at least two fiber optic sensors each comprised of bundle of optical fibers coupled to an image processing module and oriented towards a scanning area of sealed packages moving through a conveyance system. Block 420 provides the step of processing images of sealing areas captured by the multi-head optical scanner to determine if the sealing areas contain artifacts therein. Then Block 430 provides the step of identifying sealing areas including sealing area locations wherein artifacts are located within sealed sterile packages.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. An inspection station for optically inspecting sealed packages to identify artifacts in sealing areas defining a boundary and inspection area of two sides and a top and bottom surrounding at least one sterile object contained within the sealed packages, comprising:
   a multi-head optical scanner including: a first set of an at least two fiber optic sensor arrangement with each set comprising more than one optical fiber from a bundle of optical fibers arranged into a linear face and mounted on a conveyance system to acquire optical feedback of the sealing areas moving linearly in a y-direction that is parallel with movement of the conveyance system and that are located on each of the two sides of the at least one sterile object contained in sealed packages during movement of the conveyance system, and a second set of an at least two fiber optic sensor arrangement with each set comprising more than one optical fiber from a bundle of optical fibers arranged into a linear face and mounted on a movable axis above the conveyance system to provide scanning of sealed areas along a x-direction that is perpendicular to the motion of the conveyance system and to acquire optical feedback of the sealing areas of the boundary and inspection area oriented in the x-direction with respect to movement of the conveyance system, wherein boundary areas of the sealing areas targeted by the second set are located on top and bottom of the at least one sterile object contained in sealed packages, wherein the optical feedback is received from the sealing areas by the two sets of multi-head optical scanners as the sealed packages move through a conveyance system located beneath the multi-head optical scanners; and an image processing module analyzing input from the two sets of at least two fiber optic sensor arrangements to identify whether artifacts exist in the sealing areas of the sealed packages defining the boundary surrounding at least one sterile object contained within the sealed packages.

2. The inspection station of claim 1, further comprising an area face combining input from the at least two fiber optic sensor arrangements of each set into an array prior to providing input from the at least two fiber optic sensors to the image processing module for analysis.

3. The inspection station of claim 2, wherein said area face includes a 2×D area face combining input from the at least two fiber optic sensor arrangements into an array prior to providing the input from the at least two fiber optic sensors to the image processing module for analysis.

4. The inspection station of claim 3, further comprising a controller coupled to the image processing module to provide a control signal identifying a faulty package once artifacts in the sealing areas of a package are identified.

5. The inspection station of claim 3, further comprising a controller coupled to the image processing module to provide a control signal identifying a faulty package once artifacts in the sealing areas of a package are identified.

6. The inspection station of claim 1, further comprising a controller coupled to the image processing module to provide a control signal identifying a faulty package once artifacts in the sealing areas of a package are identified.

7. A method of inspecting sealed sterile packaging for artifacts trapped within sealed areas defining a boundary including two sides and a top and bottom surrounding a sealed pocket containing at least one sterile article on the sealed sterile packaging, comprising:

using a multi-head optical scanner to optically capture images of sealing areas on sealed sterile packages traveling in a y-direction along a conveyance system using a first set of at least two fiber optic sensors each comprised of a bundle of optical fibers coupled to an image processing module and oriented towards a scanning area located at the sides of the sealed pocket of sealed packages to acquire optical feedback from sealing areas defining a sealed pocket on the sealed packaged containing at least one sterile object, wherein the optical feedback is received from the sealing areas by the multi-head optical scanner as the sealed packages move through a conveyance system;

using the multi-head optical scanner to optically capture images of sealing areas on sealed sterile packages oriented in a x-direction perpendicular with travel of the conveyance system using a second set of at least two fiver optic sensors mounted to a movable axis above the conveyance system and including, the at least two fiber optic sensors of the second set each comprised of a bundle of optical fibers coupled to the image processing module and oriented towards a scanning area located at the top and bottom of the sealed pocket of sealed packages to acquire optical feedback from sealing areas defining a sealed pocket on the sealed packaged containing at least one sterile object, wherein the optical feedback is received from the sealing areas by the multi-head optical scanner as the sealed packages move through a conveyance system;

processing images of sealing areas captured by the multi-head optical scanner to determine if the sealing areas contain artifacts therein; and identifying sealed sterile packages including sealing area locations of sealing areas thereon wherein artifacts are located.

8. The method of claim 7, further comprising the step of providing a control signal when artifacts are identified.

9. The method of claim 7, wherein images of sealing areas are captured by the multi-head optical scanner as the sealed sterile packages move along an axis of a package conveyance system.

10. The method of claim 8, wherein images of sealing areas are captured by the multi-head optical scanner as the sealed sterile packages move along an axis of a package conveyance system.

11. The method of claim 9, further comprising the step of providing a control signal when artifacts are identified.

* * * * *